United States Patent [19]

Juvet, Jr. et al.

[11] 3,967,931
[45] July 6, 1976

[54] FLAME AEROSOL DETECTOR FOR LIQUID CHROMATOGRAPHY

[75] Inventors: Richard S. Juvet, Jr., Phoenix, Ariz.; Richard A. Mowery, Jr., Bartlesville, Okla.

[73] Assignee: Research Corporation, New York, N.Y.

[22] Filed: Sept. 25, 1974

[21] Appl. No.: 509,258

[52] U.S. Cl. .......................... 23/230 PC; 23/232 C; 23/253 PC; 23/254 EF
[51] Int. Cl.² .................. G01N 31/08; G01N 31/12
[58] Field of Search .... 23/230 PC, 253 PC, 254 EF, 23/232 E

[56] References Cited
UNITED STATES PATENTS

| | | |
|---|---|---|
| 3,585,003 | 6/1971 | Scolnick .......................... 23/254 EF |
| 3,775,058 | 11/1973 | Bush .......................... 23/232 C X |
| 3,814,583 | 6/1974 | Miller et al. ................. 23/254 EF X |
| 3,840,343 | 10/1974 | Riedmann .................... 23/254 EF |
| 3,850,579 | 11/1974 | Dubsky .......................... 23/254 EF |

Primary Examiner—Robert M. Reese
Attorney, Agent, or Firm—Oblon, Fisher, Spivak, McClelland & Maier

[57] ABSTRACT

A sensitive universal detector for liquid chromatography is disclosed in which eluent from a liquid chromatograph column is aspirated into a flame and broken into a fine spray of aerosol particles. Water, when used as the mobile phase, is not ionized appreciably by the flame but does form charged droplets by rupturing of the liquid surface. The solute, when desolvated and burned in the flame, forms ionized species which affect the amount of charge on the aerosol particles. The aerosol particles, partially desolvated and ionized by the burner flame, move upward toward a filter electrode which removes gas phase ionic species from the particle stream. The charged, undesolvated aerosol particles passing the filter electrode enter an evacuated detection chamber in which a pair of detector electrodes is positioned. An electrometer system senses a varying current between the detector electrodes as each solute is eluted from the column.

22 Claims, 8 Drawing Figures

FLAME AEROSOL DETECTOR FOR LIQUID CHROMATOGRAPHY

ORIGIN OF THE INVENTION

The invention described herein was made in the course of or under a grant from the National Science Foundation, an Agency of the United States Government.

BACKGROUND OF THE INVENTION

1. Field of the Invention:

This invention relates generally to liquid chromatography, and more particularly to a flame aerosol detector and a method for using the same.

2. Description of the Prior Art:

A variety of detector systems for use in liquid chromatography are known at the present time. These presently known devices have sought, through reliance upon different sensing techniques, to achieve the illusive goal of providing a detector that is both universal and extremely sensitive.

A brief summary of such previously known devices is presented in co-pending application, Ser. No. 483,297, filed June 26, 1974. This same application describes a novel liquid chromatography detector and a novel method of detection for sensing solutes through a spray impact technique. Although the method and apparatus described in this co-pending application have proven to be extremely sensitive, the sensitivity is greatest for such compounds as fatty acids, phenols, detergents of the alkylsulfonate type, amino acids, amines, inorganic acids, bases, and salts. The spray impact detector is somewhat less sensitive to nonionic organic compounds, particularly those of low molecular weight.

A need therefore exists for a detector of substantially universal application combined with high sensitivity.

SUMMARY OF THE INVENTION

Accordingly, it is one object of this invention to provide a novel method of detecting solutes in liquid chromatography.

Another object of the present invention is the provision of a novel apparatus for detecting solutes in liquid chromatography.

A still further object of the present invention is the provision of a novel flame aerosol detector for liquid chromatography.

A still further object of the present invention is the provision of a novel flame aerosol detector including an apparatus for removing unwanted ionic species from a charged aerosol spray.

Yet another object of the present invention is the provision of a novel method of detecting solutes in liquid chromatography including the step of removing undesired ionic species from a charged aerosol spray.

Briefly, these and other objects of the invention are achieved by providing a detector including a burner flame into which the eluent of a liquid chromatography system is aspirated. A filter electrode is placed above the burner flame for removing unwanted gas phase ionic species from the rising particle stream emerging from the flame. An evacuated detection chamber, having a small aperture positioned above the flame, is provided for collecting charged aerosol particles passing the filter electrode. A pair of electrodes positioned within the chamber is coupled to an electronic network for sensing the current flow in the chamber which varies as solutes reach the detection chamber.

BRIEF DESCRIPTION OF THE DRAWINGS

A more complete appreciation of the invention and many of the attendant advantages thereof will be readily obtained by reference to the following detailed description when considered in connection with the accompanying drawings, wherein.

DESCRIPTION OF THE PREFERRED EMBODIMENTS

Figure 1:
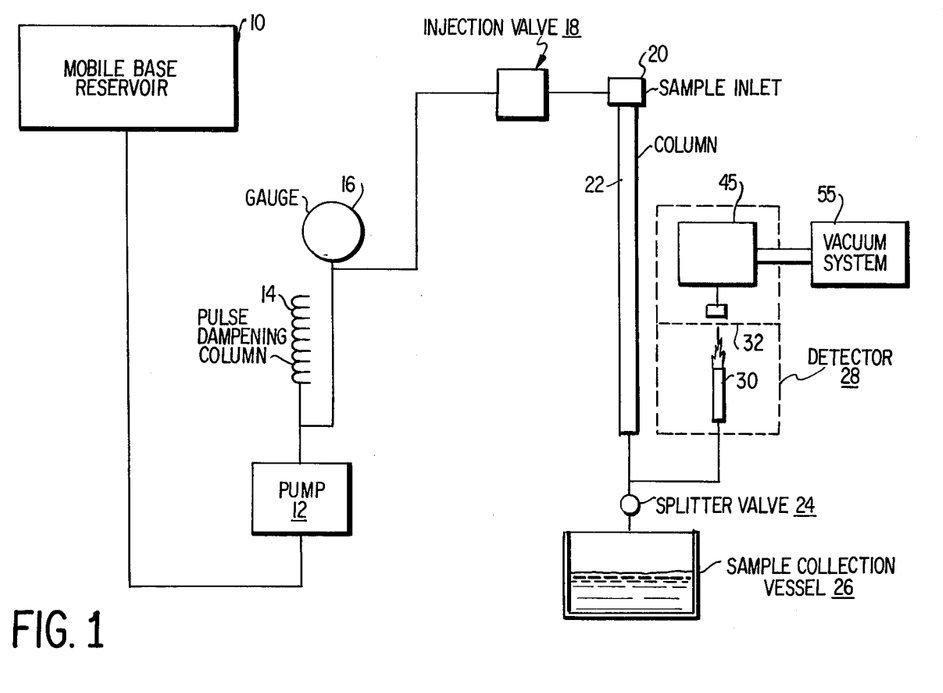
FIG. 1 is a schematic diagram of a liquid chromatography system having the detector of the present invention attached thereto.

Referring now to the drawings, wherein like reference numerals designate identical or corresponding parts throughout the several views, and more particularly to FIG. 1 thereof, a liquid chromatograph system is shown illustrating the environment of the present invention. The illustrated liquid chromatograph system includes a mobile phase reservoir 10 coupled to a pump 12 having a pulse dampening column 14 connected to the output thereof. A pressure gauge 16 is coupled between the output of pump 12 and an injection valve 18, which is in turn connected to a sample inlet 20 at the top of liquid chromatographic column 22. It is noted that samples may be introduced either by injection of microliter amounts by syringe at the sample inlet 20 or by using a sample loop containing dilute solution at the injection valve 18. Thus either the injection valve or the sample inlet may be omitted from the system if desired. The base of the chromatographic column 22 may be coupled to a splitter valve 24 which divides the column output between a sample collection vessel or waster container 26 and the detector 28 constructed in accordance with the teachings of the present invention.

The illustrated chromatography system is conventional and may be of the type described in *U.S. Bureau of Standards Technological Note No.* 589. Page 1 (July 1970 to June 1971) by D. H. Freeman and W. L. Zielinski modified to include a lengthened pulse dampening column so that the system is virtually pulse free at high pressures. Naturally it will be understood by those skilled in the art that the detector of the present invention is not limited to use with the particular type of liquid chromatograph system shown, and can be used with virtually any commercially available system.

Figure 2:
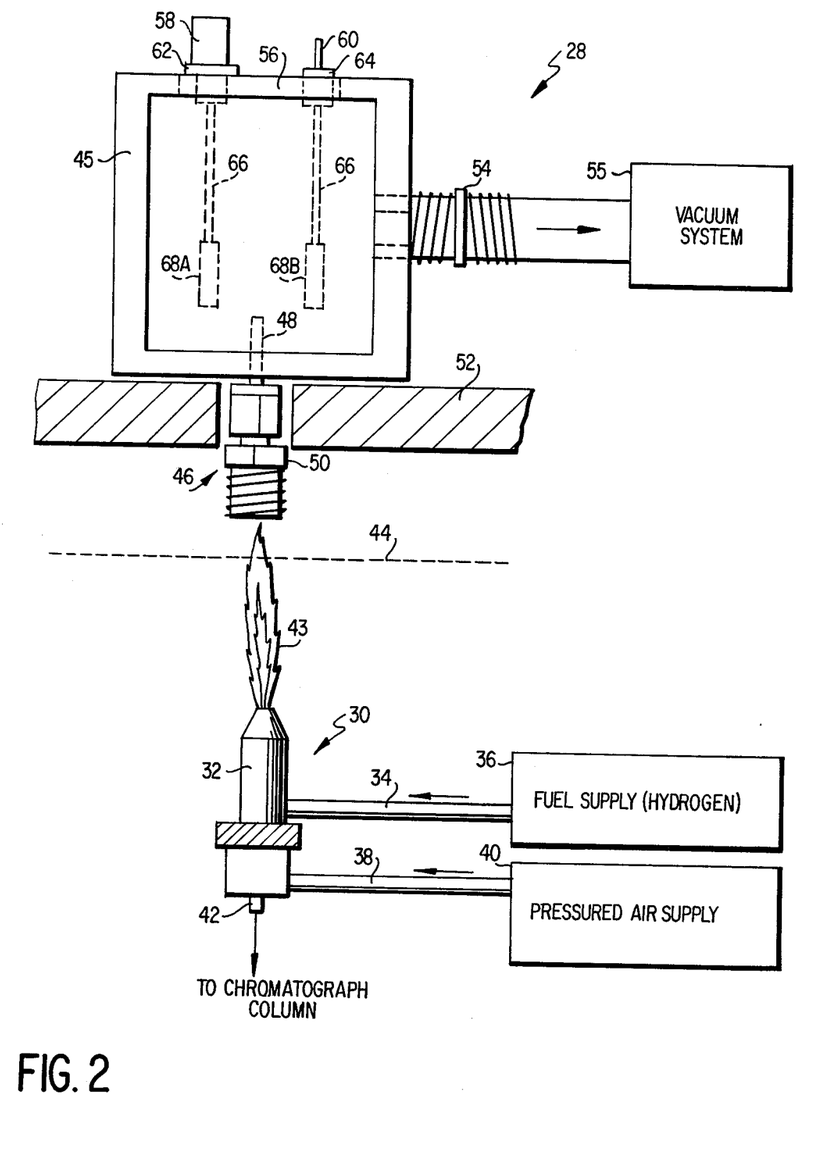
FIG. 2 is a partially cut-away illustration of the detector structure of the present invention showing more clearly the structural details thereof.

Attention is now directed to FIG. 2 wherein the flame aerosol detector of the present invention is shown in greater detail as including a conventional burner 30 for producing a charged aerosol spray in the flame as described below. The burner includes a barrel portion 32 having three inlet tubes connected to its base portion. These include a fuel inlet 34 connected to a supply 36 of suitable burner fuel, such as hydrogen, an air inlet 38 connected to a suitable supply of pressurized air or oxygen 40 and a column effluent inlet 42, connected to the output of the chromatograph column 22 illustrated in FIG. 1.

Figure 7:
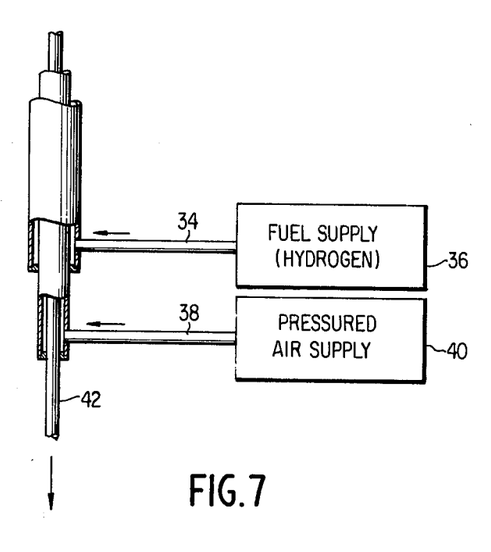

In practice the inlets 34, 38 and 42 may be formed of stainless steel tubes arranged in a concentric configuration with the mobile phase inlet at the center surrounded by the air inlet so that the high velocity incoming air flow both aspirates the liquid chromatograph output into the burner and divides it into fine aerosol particles. The fuel inlet preferably surrounds the air inlet. The air or oxygen inlet tube 38 may have an inner diameter of approximately 0.08 cm., the fuel inlet 34 an inner diameter of approximately 0.20 cm. and the mobile phase inlet 42 an inner diameter of approximately 0.04 cm. and an outer diameter of approximately 0.07 cm.

The aerosol formed as described above is propelled into the flame 43 resulting from combustion of the mentioned fuel-air mixture, where a portion of the aerosol particles desolvate and solute, if present, burns and is ionized. Larger droplets pass through the flame without complete desolvation.

A filter electrode 44 for removing desolvated ionic species is mounted above the flame 43 directly in the path of the rising aerosol stream. The filter electrode may be formed of either a loop of inert metal, such as platinum wire, a screen of inert metal or a section of 20-mesh copper screen, although other electrode materials, mesh size, and configurations may also be used.

A detection chamber 45 is positioned above the filter electrode 44 and includes an aerosol inlet assembly 46 positioned directly above flame 43. The detection chamber may, for example, be formed of a copper cylinder of approximately 2 inches inner diameter, although other structures may also be used. The aerosol inlet assembly 46 may include a length of ⅛ inch stainless steel tubing having an inner diameter of approximately 0.2 cm. and extending approximately 0.8 cm. into the chamber 45 for limiting the size of particles admitted to the detection chamber. The tube 48 is connected to a component 50 having an enlarged opening for funneling aerosol particles emerging from flame into the chamber 45. The component 50 may, for example, be a standard Swagelok reduction union joined to the tube 48, although other types of equivalent fittings can also be used. A heat shield 52, which may be constructed of asbestos, is positioned below the detection chamber to insulate it from the heat of the burner flame.

A vacuum union 54 is mounted in the peripheral wall of the detection chamber for coupling the interior of the chamber with a conventional vacuum system 55, such as a pump or water aspirator, for example. The top of the detection chamber is sealed with a copper disc 56 in which two electrical connectors 58 and 60 are mounted by means of a pair of insulating plugs 62 and 64, respectively, formed of Teflon (TM) or the like. The electrical connectors 58 and 60 are coupled by means of a pair of conductive leads 66 to a pair of detector electrodes 68A and 68B positioned within the detection chamber and spaced approximately 1 inch apart. Other spacings may also prove useful, as will be apparent to those skilled in the art. The detector electrodes may, for example, be formed of ½ inch wide by 1 inch long panels of palladium-silver alloy or other conducting material.

Figure 3:
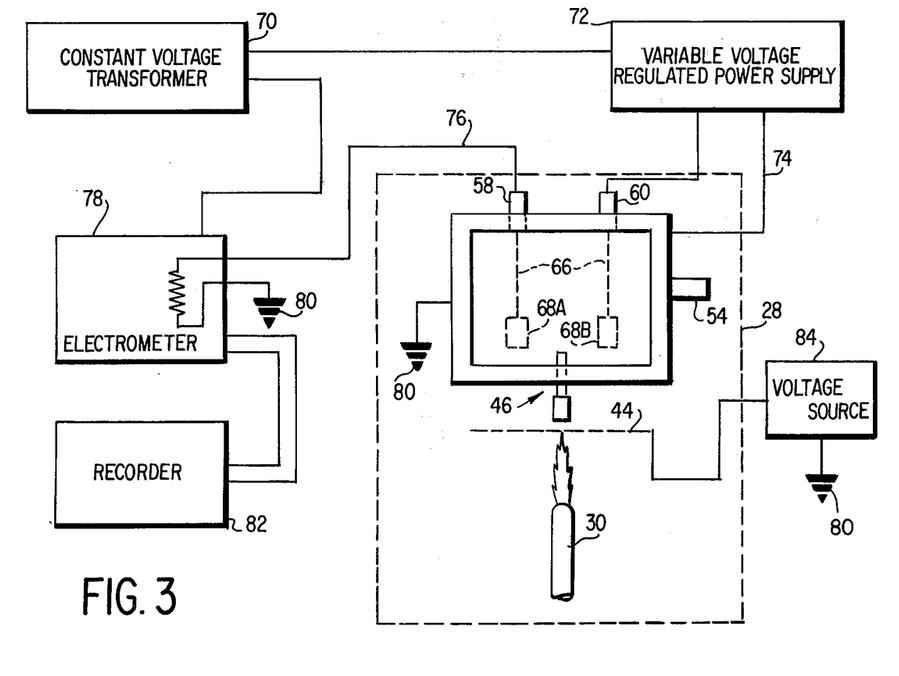
FIG. 3 is a block diagram of the electrical system of the present invention.

The varying current flowing between the electrodes 68A and 68B is sensed and recorded by the electrical network illustrated in FIG. 3 for providing a suitable output from the detector 28. The electrical network illustrated in FIG. 3 includes a conventional constant voltage transformer 70 adapted to be plugged into a normal 110 volt AC wall outlet. A variable voltage regulated power supply 72, which may be a Heath Model PS-3 for example, receives its input power from the constant voltage transformer and is coupled at its output to electrical connector 60 for supplying an input potential to the detector electrode 68B in the detection chamber. While input potentials between 150 and 700 volts with respect to ground provide a suitable output response with the geometry described, the detector electrode is preferably maintained at a constant 400 volts with respect to ground for optimum detector response. A lead 74 is provided for grounding the variable voltage supply 72 through the detection chamber ground 80.

Detector electrode 68A and electrical connector 58 are coupled by coaxial cable 76 to a conventional electrometer 78, such as a Keithley Model 603. The electrometer and the detection chamber are also coupled to a suitable reference potential, such as ground, as illustrated at 80. The electrometer output is applied to a conventional chart recorder 82, a Sargent Model MR recorder, for example, in order to continuously record the output of the electrometer. A suitable voltage source 84 is coupled to the filter electrode 44 for supplying a filtering potential thereto. The voltage source 84 may be a commercially available source, such as a Heath Model MP-5 power supply, or it may be a constant voltage source for supplying a fixed voltage such as ± 100v with respect to ground.

Figure 4A:
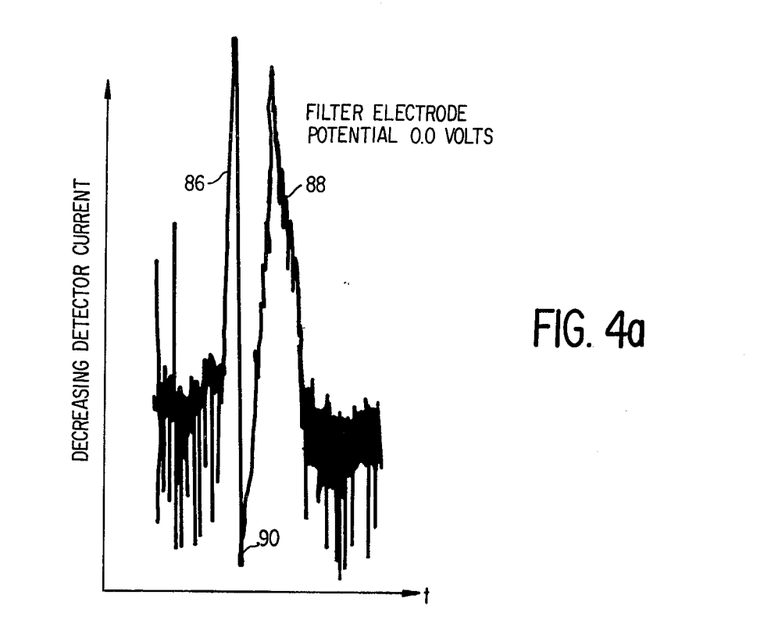
FIG. 4A is a graph illustrating the output of the detector of the present invention with no potential applied to the filter electrode.
Figure 4B:
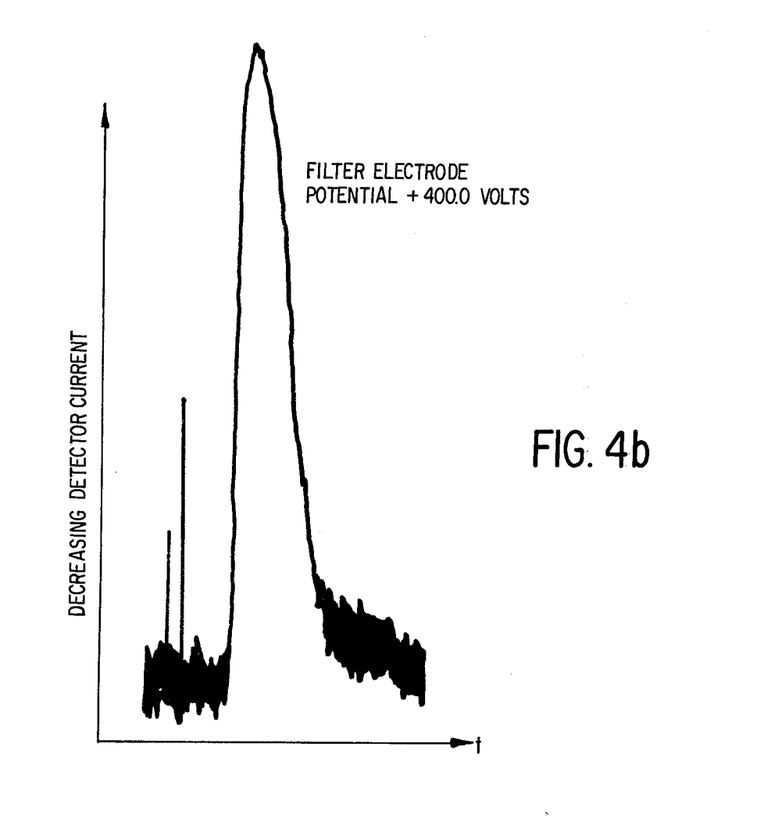
FIG. 4B is a graph illustrating the output of the detector of the present invention with a potential of 400 volts with respect to ground applied to the filter electrode.

The filter electrode is an important feature of the present invention in that it substantially increases the sensitivity of the detector and improves peak shape as shown in FIGS. 4A and 4B illustrating detector response as a function of time with and without an applied filter electrode potential. More specifically, FIG. 4A illustrates that with no applied filter electrode potential, the detector upon sensing a solute may generate an output signal having a split positive peak 86 and 88 separated by a substantial negative peak 90. The resultant output signal is thus ambiguous and has a lower signal-to-noise ratio than that in FIG. 4B. FIG. 4B illustrates the detector output current when a positive potential of 400 volts with respect to ground is applied to the filter electrode. FIG. 4B shows a single major positive peak 92 providing a clear, unambiguous output signal with a signal-to-noise ratio that is substantially greater than in the example illustrated of FIG. 4A. TABLE 1 below sets forth the experimental parameters relating to FIGS. 4A and 4B.

TABLE 1

| FIGS. 4A and 4B | |
| --- | --- |
| Electrometer setting: | 250mV full scale |
| Recorder: | 5 volts full scale |
| Potential applied to electrode 68B in detector chamber | +400 volts with respect to ground |
| Sample: | 0.5ml containing 1.56 mg/ml. n-propanol |
| Fuel flow: | approximately 2500 ml/min. (hydrogen) |
| Air flow: | approximately 5800 ml/min. |
| Liquid flow: | about 3 ml/min. |
| Pressure in chamber | 690 torr (water aspirator) |
| Chart speed: | 3 min/in. |

Figure 5:
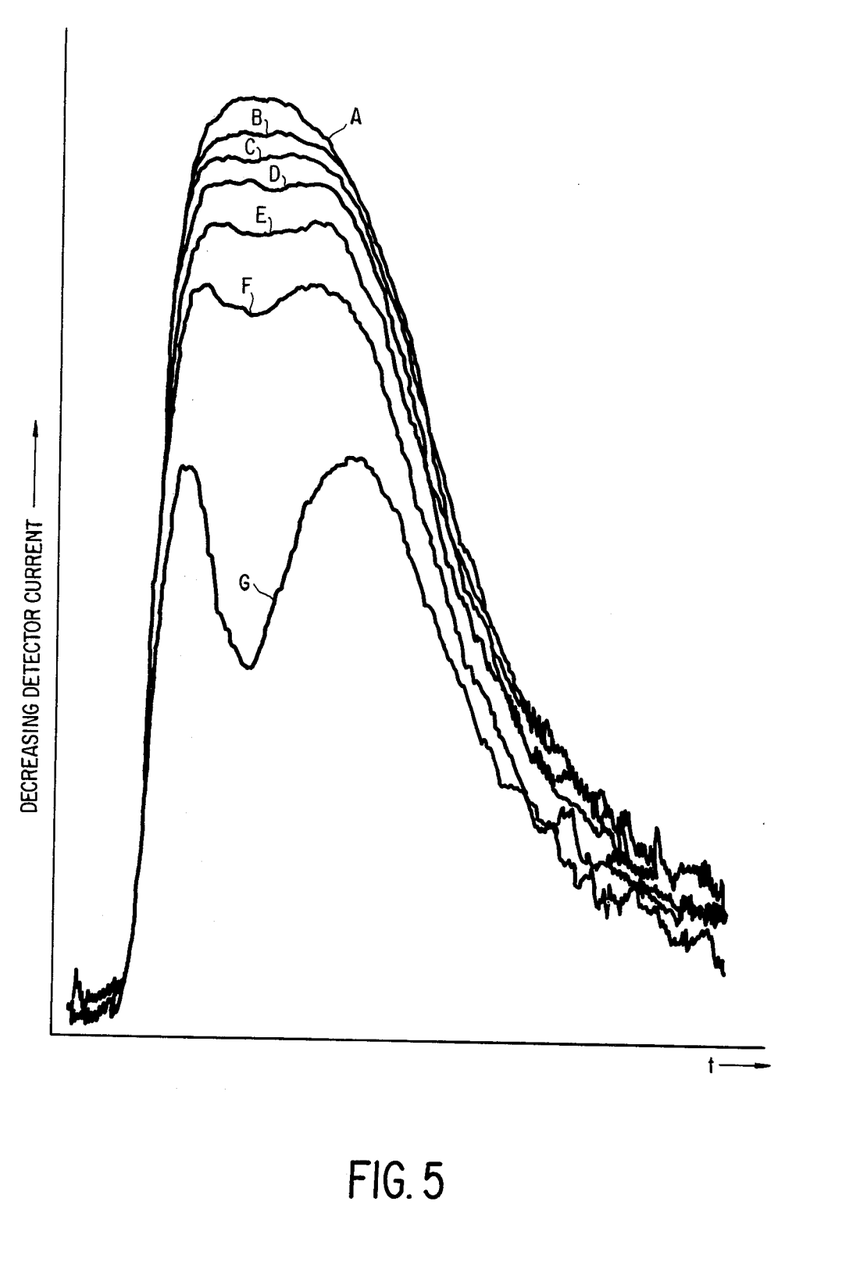
FIG. 5 is a graph at high recorder chart speed illustrating the output of the detector of the present invention with various positive potentials applied to the filter electrode.
Figure 6:
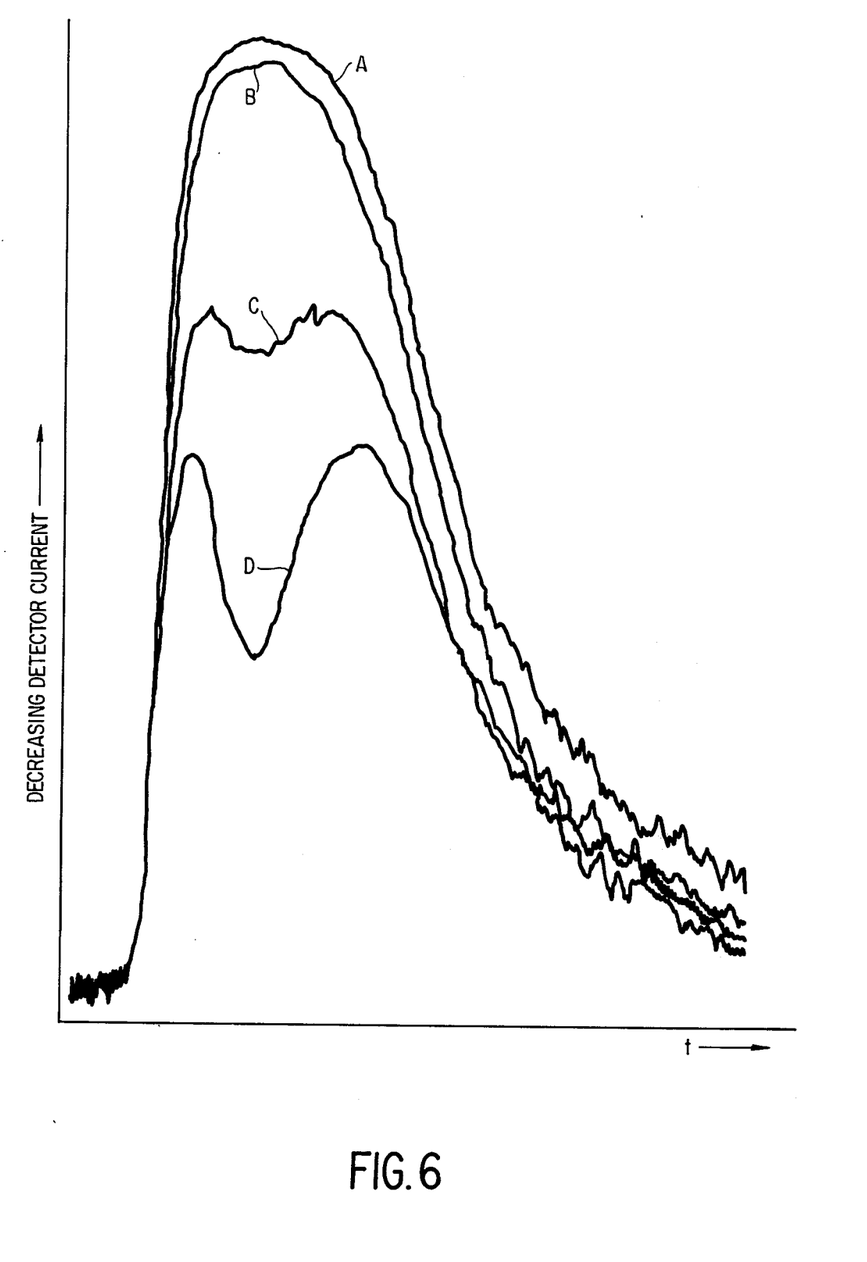
FIG. 6 is a graph at high recorder chart speed illustrating the output of the detector of the present invention with various negative potentials applied to the filter electrode and, FIG. 7 is an illustration of a concentric arrangement for the fuel, air and effluent tubes.

The effectiveness of the filter electrode is a function of the applied filter potential, as illustrated in FIGS. 5 and 6 and in TABLE 2 below.

TABLE 2

| FIGS. 5 and 6 | |
| --- | --- |
| Potential applied to electrode 68B in detection chamber: | +400 volts with respect to ground |
| Sample: | 0.5 ml. containing 1.56 mg/ml. n-propanol |
| Chart speed: | high speed—30 sec/in. |
| Pressure in detector chamber | 695 torr (water aspirator) |

| FIG. 5 | FIG. 6 |
| --- | --- |
| Filter electrode potential: (with respect to ground) | Filter electrode potential: (with respect to ground) |
| Peak A: + 100 volts | |
| Peak B: + 200 volts | |
| Peak C: + 400 volts | |
| Peak D: + 30 volts | Peak A: − 100 volts |
| Peak E: + 20 volts | Peak B: − 25 volts |
| Peak F: + 10 volts | Peak C: − 5 volts |
| Peak G: 0 volts | Peak D: volts |

FIG. 5 illustrates that an M-shaped peak G occurs when no voltage is applied to the filter electrode, and that the inverted peak diminishes rapidly as the applied voltage is increased to +100 volts with respect to ground, with a slight decrease in positive signal at higher potentials. Similarly, FIG. 6 indicates substantially the same effect with a negative voltage applied to the filter electrode. The two figures illustrate that the approximate optimum filter electrode potentials are ± 100 volts under the operation conditions listed above.

AC potentials of varying magnitudes and frequencies may also be applied to the filter electrode. Experimental results show that the application of a 60 cycle, ± 6.3 volt AC signal to the filter electrode results in filtering qualities similar to those found with a DC source of several hundred volts coupled to the filter electrode. The detection peak with this AC signal was also of substantially the same area as with the DC signals, although noise levels were slightly higher than with the DC filtering potential. Low frequency square waves of ± 180 volts at 7.5 and 11 Hz were applied to the filter electrode and also showed the filtering qualities of equivalent DC potentials. AC signals of ± 10 volts at frequencies from 100 Hz to 10kHz were also used, and the results were found to be similar to equivalent DC potentials. A ± 60 volt square wave up to 1MHz was also tried. It was found that frequencies up to about 2500 Hz provided good filtering characteristics. Frequencies above this value generally produced some loss of peak area and the M-shaped inverted peak illustrated in FIG. 4A reappeared although some filteration was present since the inverted peak was reduced to about half of its no signal level.

Although adjustments in the filter electrode potential have a pronounced effect on the response of the detector of the present invention, the operating parameters of the detection chamber 45 and the vacuum system 55 also influence output response.

The temperature of the detection chamber has an effect on the sensitivity of the detector, for example. The detection chamber is insulated from the burner flame by a board of asbestos, or an equivalent material, as pointed out above, in order to prevent the temperature of the detection chamber from exceeding the melting point of the Teflon plugs 62 and 64. The response of the detector has been found to increase with detection chamber temperature, reaching a maximum when the chamber reaches its stable equilibrium temperature.

Electrode spacing within the detection chamber affects the response of the system, and may be varied from the one inch spacing mentioned above, although a spacing of one inch appears to provide an optimum response with a relatively low noise level and a relatively high output stability with the detector geometry illustrated in FIG. 2.

Similarly, the vacuum maintained within the detection chamber affects the response of the system. Little current flows in the detector chamber without some reduction in pressure; the amount of current flow increasing as the chamber pressure is reduced, although noise also increases with reduced pressure. A water aspirator maintaining the chamber pressure between 690 and 700 torr produced suitable performance. Mechanical pump vacuum systems can be used to further reduce the detection chamber pressure.

Having described the apparatus of the present invention, its method of operation will now be described in greater detail.

It is initially assumed that the fuel and air supplies to the burner 30 are operating, that the burner is lit and that the electrical and chromatograph systems are functioning in their normal, stable state. A sample to be analyzed is then injected into the sample inlet 20 for passage through the liquid chromatograph column 22. The eluent emerging from the base of the column is divided by the splitter valve 24 with a selected fraction of the eluent being delivered to the sample collection vessel 26 and the remaining fraction being supplied to the burner 30.

The eluent delivered to the burner is aspirated into the flame by the high velocity air stream supplied to the burner. Aspiration of the eluent liquid causes it to be broken into small droplets, forming an aerosol within the flame. When the aerosol is formed of an organic compound mixed in a mobile phase such as water, the flame burning the aerosol produces ions by the chemi-ionization process. This causes a sudden increase in ion concentration within each aerosol droplet as well as an increase in evaporation and reduction in surface tension along the liquid-gas interface. As a result the aerosol particles tend to explode into a shower of smaller particles which, along with completely desolvated ionic species, move toward the filter electrode.

The filter electrode removes the highly mobile, desolvated ionic species from the stream of undesolvated, charged droplets passing through the flame and thus prevents these gas phase ions from entering the detection chamber. Removal of these gaseous ions from the particle stream is believed to be responsible for the elimination of the negative peak 90 shown in FIG. 4A. The charged droplets remaining in the particle stream are largely unaffected by the filter electrode potential owing to their relatively large mass and momentum.

Charged droplets passing the filter electrode enter the enlarged inlet component 50 and proceed upward into the detection chamber 45 under the influence of their initial momentum as well as under the influence of the reduced pressure within the chamber. Some of the charged droplets collide with the walls of the inlet tube and are grounded, while remaining droplets of appropriate dimensions travel the distance of the inlet tube and reach the region of the electrodes 68A and 68B. Thus the inlet tube sorts the droplets to some extent, and passes only those aerosol particles with dimensions within the limited range.

When droplets enter into the detection chamber they have attained a relatively high velocity and at the same time are subjected to the hot, reduced pressure environment of the chamber as well as to the force field of the electrodes. These forces, combined with the force of gravity which normally acts on them, cause the aerosol particles within the chamber to become an extremely finely divided charged mist. This fine charged mist causes the current flow between the electrodes which fluctuates in response to the presence of the desolved solutes injected into the chromatograph system. Other mechanisms, yet not fully understood, may also provide or contribute to the change in signal observed as the solutes are eluted.

When an organic compound is eluted, increased evaporation, instability of the droplet, and several other processes cause a much smaller initial droplet. This brings about a significant decrease in the number of particles reaching the chamber with a decrease in the amount of charged mist and current flow. The varying current is detected by the electrical system of the present invention, whereby output peaks are produced as solute components reach the detector electrodes.

Tests with n-propanol show that a plot of log (peak area) vs. log concentration is linear over at least five orders of magnitude while other commercial detectors are rarely linear more than 3-4 orders of magnitude. The lower limit of detection for n-propanol was found to be 64 ng/ml (64 parts per billion), far exceeding the limit of detection of n-propanol with other detectors presently commercially available. Furthermore the detector of the present invention was found to produce an increasing response with an increase in carbon number so that even lower detection limits are found for compounds of higher molecular weight. Among the other compounds studied and found to give high sensitivity are dimethyl sulfoxide, sulfanilic acid, p-toluidine, benzene, resorcinol, benzyl disulfide, caffeine, thioacetamide, benzyl alcohol, 1,4-butanediol, alanine, aspartic acid, ethyl butyrate, potassium chloride, and an homologous series of alchols from methyl alcohol to heptyl alcohol. All compounds tested give a signal upon elution, and it is believed that the flame aerosol detector is truly a universal detector.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of detecting components eluted from a liquid chromatograph comprising the steps of:
   producing a liquid aerosol from a liquid sample eluted from said chromatograph,
   ionizing at least a portion of said liquid aerosol,
   filtering said ionized liquid aerosol to remove unwanted ionic species; and,
   sensing variations in the current formed by the ionized liquid aerosol subsequent to said step of filtering whereby said components are detected.

2. A method as in claim 1, wherein said step of producing includes the step of:
   aspirating said liquid sample with a stream of high velocity gas whereby said liquid sample is broken into small aerosol droplets.

3. A method as in claim 1, wherein said step of ionizing includes the step of:
   passing said liquid aerosol through a flame.

4. A method as in claim 1, wherein said step of sensing includes the steps of:
   positioning at least two electrodes in an enclosure having an opening for receiving said ionized liquid aerosol,
   maintaining said electrodes at different potentials relative to one another so that said ionized liquid aerosol forms a current between said electrodes;
   at least partially evacuating said enclosure to enhance current flow between said electrodes; and
   monitoring said current for detecting variations therein which provide an indication of the presence of said components.

5. A method as in claim 1, wherein said step of filtering includes the step of:
   passing said ionized liquid aerosol through an electrode having an electrical filtering potential applied thereto.

6. A method as in claim 5, further comprising the step of:
applying a positive d.c. voltage to said electrode as said filtering potential.

7. A method as in claim 5, further comprising the step of:
applying a negative d.c. voltage to said electrode as said filtering potential.

8. A method as in claim 5, further comprising the step of:
applying an a.c. voltage to said electrode as said filtering potential.

9. An apparatus for detecting components eluted from a liquid chromatograph comprising:
aspirating means for producing a liquid aerosol from a liquid sample eluted from said chromatograph,
ionizing means positioned adjacent said aspirating means for receiving and at least partially ionizing said liquid aerosol,
filtering means positioned adjacent said ionizing means for subjecting said ionized liquid aerosol to an electrical field for removing unwanted ionic species therefrom; and,
sensing means for detecting variations in the current formed by ionized liquid aerosol particles passing said filtering means.

10. An apparatus as in claim 9, wherein said sensing means comprises:
an enclosure, said enclosure having an inlet means therein for receiving ionized liquid aerosol particles;
a pair of current sensing electrodes mounted in spaced relationship inside said enclosure,
voltage source means for supplying a biasing voltage to at least one of said sensing electrodes; and,
electronic means for measuring current flow between said electrodes.

11. An apparatus as in claim 10, further comprising:
evacuating means coupled to said enclosure for maintaining the interior of said enclosure below atmospheric pressure.

12. An apparatus as in claim 11, wherein said electronic means comprises:

an electrometer coupled to one of said sensing electrodes.

13. An apparatus as in claim 11, wherein said inlet means comprises:
an inlet tube of a predetermined interior diameter for limiting the size of particles permitted to enter said enclosure; and,
a funneling means for directing said ionized aerosol particles toward said inlet tube.

14. An apparatus as in claim 13, further comprising;
insulating means positioned between said enclosure and said ionizing means for shielding said enclosure from heat produced by said ionizing means.

15. An apparatus as in claim 9, wherein:
said ionizing means comprises a burner; and,
said aspirating means comprises a plurality of tubes coupled to said burner for supplying liquid from said chromatograph, high pressure aspirating gas and fuel to said burner.

16. An apparatus as in claim 15, wherein:
said tubes are arranged concentrically for efficiently forming said liquid aerosol and mixing said aerosol, said high pressure gas and said fuel.

17. An apparatus as in claim 15, wherein said filtering means comprises:
an electrode placed in the path of liquid aerosol particles emerging from said ionizing means; and,
power supply means coupled to said electrode for applying a suitable filtering potential thereto.

18. An apparatus as in claim 17, wherein:
said electrode comprises a screen formed of an inert metal.

19. An apparatus as in claim 17, wherein:
said electrode comprises a loop of wire formed of an inert metal.

20. An apparatus as in claim 17, wherein:
said power supply means comprises a source of negative d.c. voltage.

21. An apparatus as in claim 17, wherein:
said power supply means comprises a source of positive d.c. voltage.

22. An apparatus as in claim 17, wherein:
said power supply means comprises a source of a.c. voltage.

* * * * *